(12) United States Patent
Hollander et al.

(10) Patent No.: US 6,454,569 B1
(45) Date of Patent: Sep. 24, 2002

(54) DENTAL IMPLANT HAVING A DUAL BIO-AFFINITY COLLAR

(75) Inventors: Bruce L. Hollander, Boca Raton; Ingo K. Kozak, Atlantis, both of FL (US)

(73) Assignee: BioLok International, Inc., Deerfield Beach, FL (US)

( * ) Notice: Subject to any disclaimer, the term of this patent is extended or adjusted under 35 U.S.C. 154(b) by 0 days.

(21) Appl. No.: 09/605,142

(22) Filed: Jun. 26, 2000

Related U.S. Application Data

(63) Continuation-in-part of application No. 09/500,038, filed on Feb. 8, 2000, which is a continuation-in-part of application No. 08/996,244, filed on Dec. 22, 1997, now abandoned, which is a continuation-in-part of application No. 08/639,712, filed on Apr. 29, 1996, now abandoned, which is a continuation of application No. 08/390,805, filed on Feb. 15, 1995, now abandoned, which is a continuation of application No. 08/146,790, filed on Nov. 2, 1993, now abandoned.

(51) Int. Cl.[7] .................................................. A61C 8/00

(52) U.S. Cl. ....................................................... 433/173

(58) Field of Search .................................. 433/173, 174, 433/175, 201.1; 623/17.17, 17.18, 23.5, 23.76

(56) References Cited

U.S. PATENT DOCUMENTS 5,588,838 A * 12/1996 Hansson et al. ............. 433/174
5,989,027 A * 11/1999 Wagner et al. .............. 433/173

\* cited by examiner

Primary Examiner—Cary E. O'Connor
(74) Attorney, Agent, or Firm—M. K. Silverman

(57) ABSTRACT

A dental implant comprises a solid elongated body including a longitudinal axis having distal and proximal ends in which the proximal end includes a collar having an axial length in a range of about 1 to about 3 millimeters. The collar exhibits a proximal and a distal segment in which the proximal segment includes a surface texture adapted for the promotion of tissue growth and in which the distal segment includes a surface texture adapted for the promotion of osseo-integration of surrounding preferably cortical bone. Either one or the other of the sub-segments is provided with an ordered microgeometric repetitive surface pattern in the form of alternating ridges and grooves, each having a fixed or established width in a range of about 2.0 to about 25 microns and a fixed or established depth in a range of about 2.0 to about 25 microns, in which the microgeometric repetitive patterns define a guide for preferential promotion of the rate, orientation and direction of growth colonies of cells of the maxillofacial bone or tissue which is in contact with the surface pattern.

11 Claims, 2 Drawing Sheets

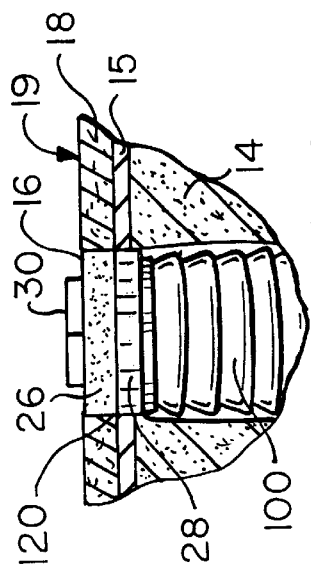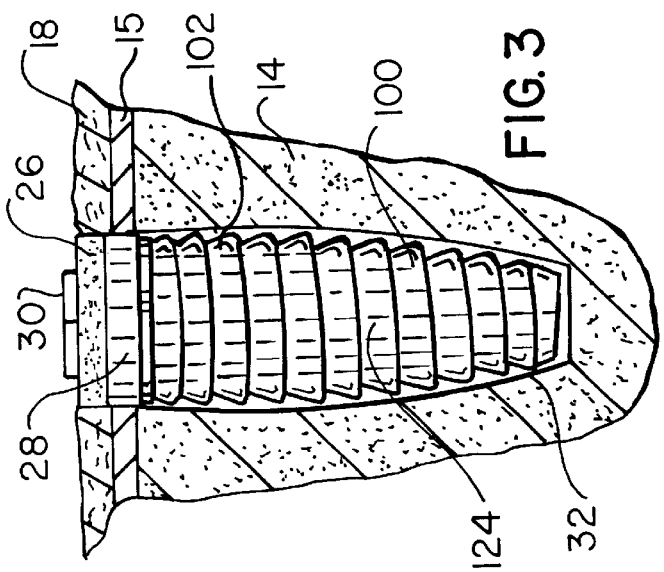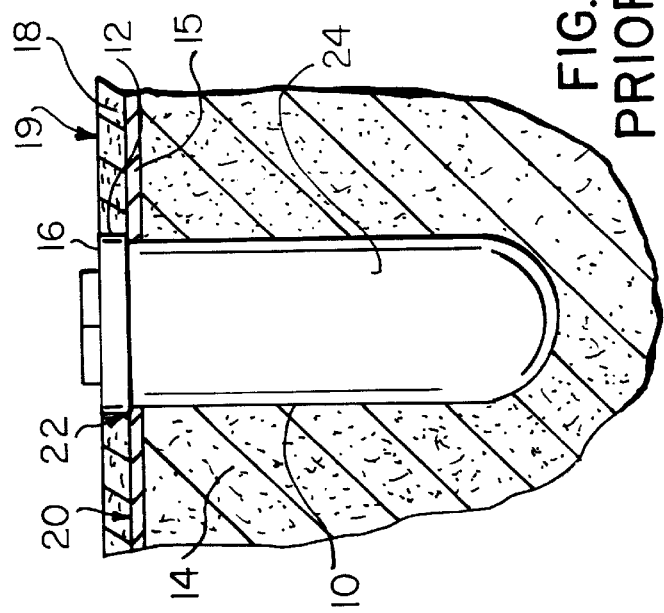

DENTAL IMPLANT HAVING A DUAL BIO-AFFINITY COLLAR

REFERENCE TO RELATED APPLICATON

This case is a continuation-in-part of application Ser. No. 09/500,038, entitled Dental Implant System with Repeating Microgeometric Surface Pattern, filed Feb. 8, 2000, pending; which is a continuation in part of application Ser. No. 08/996,244 filed Dec. 22, 1997, now abandoned; which is a continuation in part of application Ser. No. 08/639,712, filed Apr. 29, 1996, now abandoned; which is a continuation of application Ser. No. 08/390,805, filed Feb. 15, 1995, now abandoned; which is continuation of application Ser. No. 08/146,790, filed Nov. 2, 1993, now abandoned.

BACKGROUND OF THE INVENTION

The present invention relates to dental implants and, more particularly, to implants intended for insertion into the mandible, maxilla and facial bones. More particularly, the invention relates to a dental implant in which there is provided a collar having dual bio-affinity surfaces such that, in a healing process following insertion of the dental implant, the same is facilitated both with reference to bio-integration of bone and related dermal tissue which is next to the bone.

In the prior art, it is known to provide a variety of surface or texturing effects to enhance osseo-stability of the implant within bone, the same including the maxillofacial area, in the healing process. The collar or proximal portion of a dental implant plays a particularly significant role in that closure of the bone about the uppermost part of the implant is essential to assure proper sealing of the bone around the implant. An added aspect in the achievement of such sealing is also proper closure of the tissue, gum, or related dermal tissue above the bone at the point of entry. In general, if proper closure of the tissue about the plane of the upper radial surface of the implant is accomplished, proper closure of the cortical bone about the implant will follow as a matter of course. It is, accordingly, desirable to promote bio-integration of both soft tissue and hard tissue which is in interface with the dental implant after insertion into an osseotomy site. This, among other factors, will optimize the role of the implant as a base or foundation upon which the dental abutment and related prosthesis is secured.

While the prior art suggests a variety of different surface effects for various and sundry types of surgical implants, only a small subset of this art addresses the provision of any form of surface effect to dental implants for any purpose. This art, as best known to the within inventors, is represented by U.S. Pat. No. 5,011,494 to Von Recum; U.S. Pat. No. 5,057,208 to Sherry; U.S. Pat. No. 4,778,469 to Lia; U.S. Pat. No. 5,751,017 to Niznick; U.S. Pat. No. 4,320,891 to Branemark; U.S. Pat. No. 4,752,294 to Lundgren; U.S. Pat. No. 4,553,272 to Mears; and U.S. Pat. No. 5,004,475 to Vermeire.

In view of the above, no art known to the inventors, with the exception of the above-referenced parent of this application, teaches any use of multiple bio-affinity surfaces. However, said parent application does not attempt to generalize the principle of dual tissue bio-affinity surfaces as is taught herein.

SUMMARY OF THE INVENTION

The instant invention relates to a dental implant, which more particularly comprises a solid elongate body including a longitudinal axis having distal and proximal ends, in which the proximal end defines a collar having an axial length in a range of about 1 to about 3 millimeters. The collar comprises both a proximal and a distal segment in which said proximal segment exhibits a surface texture adapted for the promotion of tissue growth thereinto and in which said distal segment exhibits a surface texture adapted for the promotion of osseo-integration thereinto preferably at a cortical surface of a bone. At least one of said subsegments is provided with an ordered microgeometric repetitive surface pattern in the form or a multiplicity of alternating ridges and grooves, each having a fixed or established width in a range of about 2.0 to about 25 microns and a fixed or established depth in a range of about 2.0 to about 25 microns, in which said microgemoetric repetitive patterns define a guide for preferential promotion of the rate, orientation and direction of growth colonies of cells of maxillofacial bone or tissue which is in contact with said surface pattern.

It is accordingly an object of the invention to provide a dental implant having a collar portion consisting of proximal and distal cylindrical sub-segments, one having a surface effect adapted for the promotion of growth of soft tissue thereinto and the other adapted for the promotion of bone or hard tissue growth thereinto preferably at a cortical surface of the bone.

It is a further object to provide microgeometic surfaces which alter the growth behavior of colonies of cells attached thereto in order to preclude the cupping effect between an implant and an osseotomy site.

It is another object to provide microgeometric surfaces of the above type having cross-sectional configurations, which are preferential to particular cell or tissue types.

It is a further object to provide microgeometric implant substrate for controlling in vivo cell attachment, orientation growth, migration and tissue function and therein having dimensions preferential for the prevention of cell growth in a first-axis and for the inducement of growth along a second axis.

It is a further object to provide repetitive microgeometric texturized configurations to implants applicable in a variety of medical applications.

It is another object to provide a dental implant of the above type to facilitate a wide range of procedures in the area of dental implantology in which preclusion of the cupping effect of bone-to-bone interface is advantageous.

It is a further object of the invention to provide a dental implant of the above type to provide improved stability while reducing the possibility of complications due to infection at the implant site.

The above and yet other objects and advantages of the present invention will become apparent from the hereinafter set forth Brief Description of the Drawings, Detailed Description of the Invention, and Claims appended herewith.

BRIEF DESCRIPTION OF THE DRAWINGS

FIG. 1 is a view of the prior art as it relates to the present invention.

FIG. 2 is an elevational view of the present invention shown relative to the bone and tissue area surrounding an implant site.

FIG. 3 is a view, similar to that of FIG. 2, however showing the entire length of an implant and also showing an alternate embodiment of the invention.

DETAILED DESCRIPTION OF THE INVENTION

Figure 4:
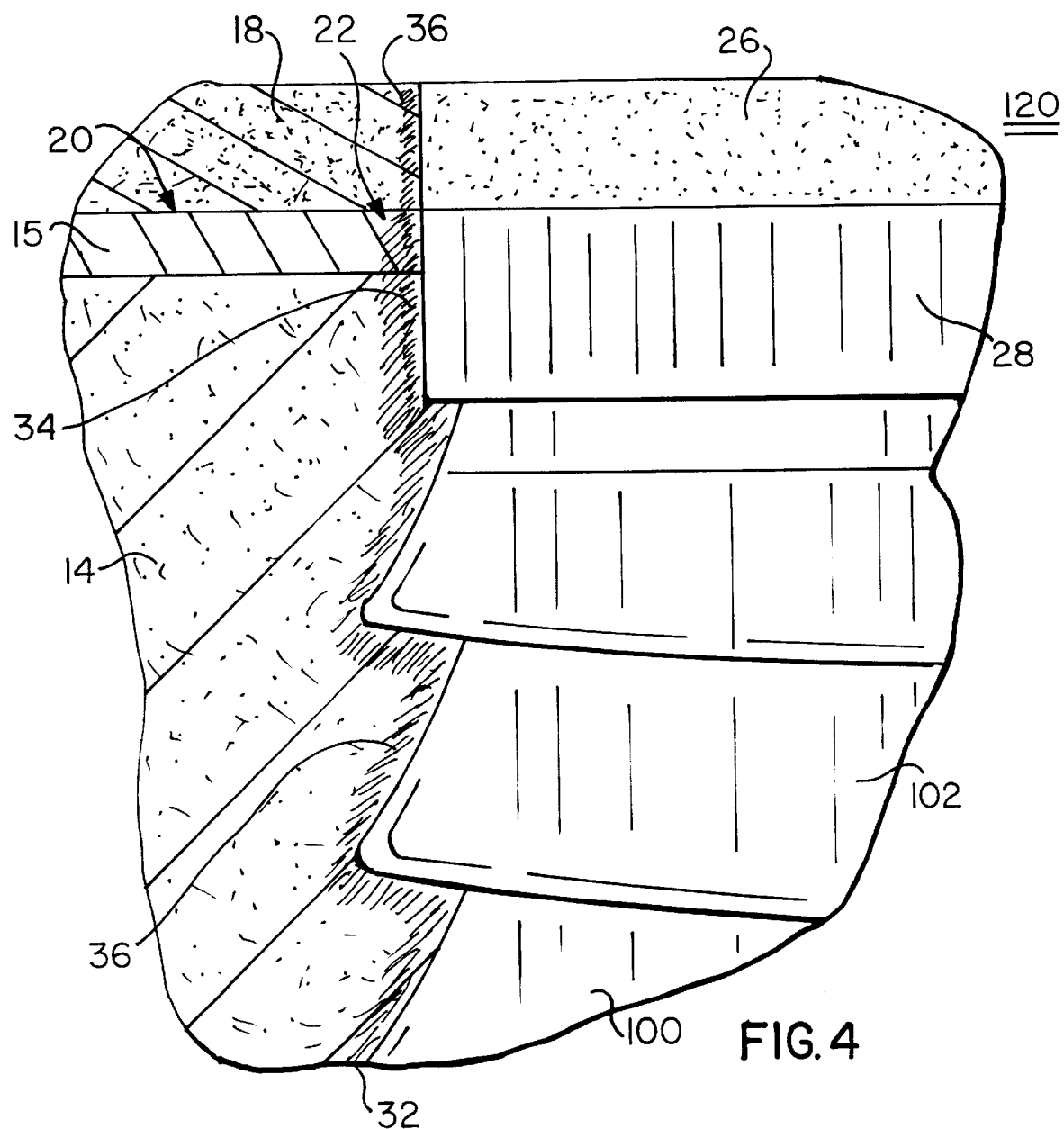
FIG. 4 is an enlarged view of the upper left hand corner of the view of FIG. 3, the same showing the area of tissue to cortical bone to implant collar interface.

With reference to FIG. 1, there is shown an example of a prior art dental implant 10 inclusive of a collar 12, and an anchor portion 24 which is positioned within bone 14 at a so-called ostectomy site. The outer or uppermost surface of bone 14 consists of a cortical bone 15 which comprises a hard shell-like layer. As noted in the Background of the Invention above, surface treatments for dental implants have been suggested only to bio-affinity of the implant relative to bone. Further, the prior art, as reflected in FIG. 1, shows an upper radial surface 16 of the collar 12 reflects the general positioning of the gum line 19 of gum tissue 18 of a patient. However, the problem with such positioning of the implant within the osseotomy site is related to an interface 20 which exists between cortical bone 15 and gum line 18, beneath said radial surface 16 of the implant collar 12. Along this interface 20 and, particularly, where this interface meets collar 16, i.e., at area 22, occurs what is termed the cupping effect at the implant interface, that is, the tendency of bone tissue to die-back from the collar 12.

The view of FIG. 2 indicates the manner in which the above problem is solved through the present invention. More particularly, shown in FIG. 2 is inventive implant 100 which has been provided with a collar 120 which includes a proximal cylindrical segment 26 and a distal cylindrical segment 28. Shown above radial surface 16 is a hex-head connection 30 which, it is to be understood, is representative of but one of a variety of means that may be used to effect securement between the implant and a dental abutment with which the implant is to mate before securement of a dental restoration thereupon.

What is notable about the structure of FIG. 2 is that two different types of bio-affinity surface effects, or textures, have been provided to the collar 120 of the implant, namely, one surface for the purpose of promoting in-growth of soft dermal or gum tissue 18 denoted by the dotted or stippled effect on proximal segment 26 and the provision of a second bio-affinity texture (denoted by the vertical hatching) upon the distal segment 28 of collar 120. Therein proximal segment 26 is axially aligned with gum tissue 18 and at least the top of distal segment is generally aligned with cortical layer 15 is of bone 14. It has been found that for optimal result, at least one of the textured surfaces should define an ordered microgeometric repetitive surface pattern in the form or a multiplicity of alternating ridges and grooves, each having a fixed or established width in a range of about 2.0 to about 25 microns and a fixed or established depth in a range of about 2.0 to about 25 microns, in which said microgeometric repetitive patterns define a guide for preferential promotion of the rate, orientation and direction of growth colonies of cells of maxillofacial bone or tissue which are in contact with said surface pattern. If both segments are furnished with such a surface pattern, the respective texture thereof will differ in that different widths and depths of texture are optimal for soft versus hard tissue interaction.

A further embodiment of the invention is shown in FIG. 3 in which an entire anchor portion 124 of the implant has been provided with the same osseo-integrative surface effect, the same indicated by reference numeral 102, as has been the distal segment 28 of the implant collar. Accordingly, in this embodiment, the entirety of an implant site below proximal segment 16 may be treated in the same fashion as the distal sub-segment 28.

With reference to the view of FIG. 4, which is an enlargement of a portion of FIG. 2, there may be seen the above-referenced proximal collar segment 26 and distal collar segment 28, as well as the optionally textured surface 102 of implant 100, the same relative to the bone 14, cortical bone 15, and soft tissue 18. However, further shown in FIG. 4 is a region 34 of osseo-integration between distal collar segment 28 and bone 14, including cortical bone 15, and a region 36 of osseo-integration between proximal segment 26 and gum tissue 18. These regions comprise in-growth of tissue 22 relative to the implant collar segments. It is to be appreciated that regions 34 and 36 of in-growth or bio-affinity between tissue 18 and segment 26 and 28 accomplish an advantageous sealing of the tissue about area 22 of the interface 20 between tissue 18 and cortical bone 15, and, particularly, at the point of entry of the collar into the cortical bone. As such, the dual affinity implant collar effectively promotes sealing of bone 22 both to implant collar 120 and, as well, sealing about the circumferential point of entry into the implant site. With such sealing the cupping effect is precluded.

If one of the collar segments 26 or 28 is not furnished with said ordered microgeometric repetitive surface matter, a variety of other surface textures may be effected for the other segments using such treatments including, without limitation, the following:

laser cutting, acid etching, photolithography, abrasion/roughening, plasma spraying, calcium sulfate, biocompatible glass, collagen, hydroxapatite, growth factor compounds, and combinations thereof.

With respect to the ratio of axial length of the proximal to the distal segments of the collar, it has been found that such axial lengths need not necessarily be equal, such that a range of axial length of the proximal to the distal segments may fall between about 1:4 to about 4:1, this within an aggregate axial length of between about 1 to about 3 millimeters.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

Having thus described our invention, what we claim as new, useful, and non-obvious and, accordingly, secure by Letters Patent of the Untied States is:

1. A dental implant for insertion into an ostectomy site, and reducing potential for related bone loss thereat, the implant comprising:

a solid elongate body having a longitudinal axis, said axis having a distal and a proximal end, said proximal end defining a collar having an axial length in a range of about 1 to about 3 millimeters, said collar further comprising a proximal segment and a distal segment in which said proximal segment comprises a surface texture for the promotion of tissue growth thereinto, and in which said distal segment comprises a surface texture for the promotion of bone growth thereinto, and further in which said distal segment defines an ordered microgeometric repetitive surface pattern in the form of a multiplicity of alternating ridges and grooves, each having a fixed or established width in a range of about 2.0 to about 25 microns and a fixed or established depth in a range of about 2.0 to about 25 microns, in which said microgemoetric repetitive patterns define a guide for preferential promotion of the rate, orientation and direction of growth colonies of cells of soft tissue of said osseotomy site which are in contact with said surface pattern.

2. The implant as recited in claim 1, in which said surface texture of said proximal segment comprises a surface texture selected from the group of surface treatments consisting essentially of:

laser cutting, acid etching, photolithography, abrasion/roughening, plasma spraying, calcium sulfate, biocompatible glass, collagen, hydroxapatite, growth factor compounds, and combinations thereof.

3. The dental implant as recited in claim 2, in which a ratio of axial length of said proximal to said distal segments comprises a range of about 1:4 to about 4:1.

4. The dental implant as recited in claim 3, in which a proximal radial surface of said implant includes means for complemental securement with a dental abutment.

5. The dental implant as recited in claim 3, in which a proximal radial surface of said implant includes means for complemental securement with a dental abutment.

6. The dental implant as recited in claim 2, in which a ratio of axial length of said proximal to said distal segments comprises a range of about 1:4 to about 4:1.

7. The implant as recited in claim 1, in which said surface texture of said distal segment comprises a surface texture selected from the group of surface treatments consisting essentially of:

laser cutting, acid etching, photolithography, abrasion/roughening, plasma spraying, calcium sulfate, bicompatible glass, collagen, hydroxyapatite, growth factor compounds, and combinations thereof.

8. A dental implant for insertion into an osseotomy site, and reducing potential for related bone loss threat, the implant comprising:

a solid elongate body having a longitudinal axis, said axis having a distal and a proximal end, said proximal end defining a collar having an axial length in a range of about 1 to about 3 millimeters, said collar further comprising a proximal segment and a distal segment in which said proximal segment comprises a surface texture for the promotion of tissue growth thereinto, and in which said distal segment comprises a surface texture for the promotion of bone growth thereinto, and further in which said proximal segment defines an ordered microgeometric repetitive surface pattern in the form of a multiplicity of alternating ridges and grooves, each having a fixed or established width in a range of about 2.0 to about 25 microns and a fixed or established depth in a range of about 2.0 to about 25 microns, in which said microgemoetric repetitive patterns define a guide for preferential promotion of the rate, orientation and direction of growth colonies of cells of bone at said osseotomy site which are in contact with said surface pattern.

9. A dental implant for insertion into an osseotomy site, and reducing potential for related bone loss threat, the implant comprising:

a solid elongate body having a longitudinal axis, said axis having a distal and a proximal end, said proximal end defining a collar having an axial length in a range of about 1 to about 3 millimeters, said collar further comprising a proximal segment and a distal segment in which said proximal segment comprises a surface texture for the promotion of tissue growth thereinto, and in which said distal segment comprises a surface texture for the promotion of bone growth thereinto, in which said proximal and distal segments define respective ordered microgeometric repetitive surface patterns in the form of a multiplicity of alternating ridges and grooves, each having a fixed or established width in a range of about 2.0 to about 25 microns and a fixed or established depth in a range of about 2.0 to about 25 microns, in which said microgemoetric repetitive patterns define a guide for preferential promotion of the rate, orientation and direction of growth colonies of cells of bone and soft tissue at said ossseotomy site which are in contact with said respective surface patterns.

10. The system as recited in claim 9, in which a ratio of axial length of said proximal to said distal segments comprises a range of about 1:4 to about 4:1.

11. The system as recited in claim 10 in which a proximal radial surface of said implant includes means for complemental securement with a dental abutment.

* * * * *

UNITED STATES PATENT AND TRADEMARK OFFICE
CERTIFICATE OF CORRECTION

PATENT NO.       : 6,454,569 B1
APPLICATION NO.  : 09/605142
DATED            : September 24, 2002
INVENTOR(S)      : Hollander et al.

It is certified that error appears in the above-identified patent and that said Letters Patent is hereby corrected as shown below:

On the face of the patent, at item (63) under "Related U.S. Application Data", delete "; which is a continuation in part of application Ser. No. 08/996,244 filed Dec. 22, 1997, now abandoned; which is a continuation in part of application Ser. No. 08/639,712, filed Apr. 29, 1996, now abandoned; which is a continuation of application Ser. No. 08/390,805, filed Feb. 15, 1995, now abandoned; which is continuation of application Ser. No. 08/146,790, filed Nov. 2, 1993, now abandoned"

At column 1, under the heading "REFERENCE TO RELATED APPLICATION", delete

", pending; which is a continuation in part of application Ser. No. 08/996,244 filed Dec. 22, 1997, now abandoned; which is a continuation in part of application Ser. No. 08/639,712, filed Apr. 29, 1996, now abandoned; which is a continuation of application Ser. No. 08/390,805, filed Feb. 15, 1995, now abandoned; which is continuation of application Ser. No. 08/146,790, filed Nov. 2, 1993, now abandoned"

Signed and Sealed this
Thirtieth Day of August, 2011

David J. Kappos
*Director of the United States Patent and Trademark Office*